US 8,323,567 B2

(12) United States Patent
Aoyagi

(10) Patent No.: US 8,323,567 B2
(45) Date of Patent: Dec. 4, 2012

(54) BIOCHEMICAL TREATMENT DEVICE WITH DISPENSING UNIT

(75) Inventor: Takaaki Aoyagi, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 294 days.

(21) Appl. No.: 11/518,245

(22) Filed: Sep. 11, 2006

(65) Prior Publication Data

US 2007/0077645 A1 Apr. 5, 2007

(30) Foreign Application Priority Data

Oct. 4, 2005 (JP) .................. 2005-291770

(51) Int. Cl.
*G01N 21/00* (2006.01)

(52) U.S. Cl. .......................... 422/67; 422/63

(58) Field of Classification Search .................. None
See application file for complete search history.

(56) References Cited

U.S. PATENT DOCUMENTS

| 4,237,096 | A   | * | 12/1980 | Popoff et al. | .................. | 422/102 |
| 6,372,185 | B1  | * | 4/2002  | Shumate et al. | ............... | 422/100 |
| 6,472,218 | B1  | * | 10/2002 | Stylli et al. | ....................... | 436/48 |
| 2003/0124599 | A1 | * | 7/2003 | Chen et al. | ......................... | 435/6 |
| 2003/0230488 | A1 | * | 12/2003 | Lee et al. | ....................... | 204/453 |
| 2007/0004029 | A1 |   | 1/2007  | Aoyagi | ...................... | 435/287.2 |
| 2007/0059817 | A1 |   | 3/2007  | Aoyagi | ...................... | 435/287.2 |

FOREIGN PATENT DOCUMENTS

| GB | 2 244 130 A | 11/1991 |
| JP | 4-230862 A | 8/1992 |
| JP | 9-96643 | 4/1997 |
| JP | 2003-274925 | 9/2003 |
| JP | 2005-37179 A | 2/2005 |
| JP | 2005-204592 A | 8/2005 |

* cited by examiner

*Primary Examiner* — Samuel Woolwine
*Assistant Examiner* — Suchira Pande
(74) *Attorney, Agent, or Firm* — Fitzpatrick, Cella, Harper & Scinto

(57) ABSTRACT

The width of reaction wells and detection wells used for the same sample in a nozzle line direction is made to fall within an area smaller than the pitches of nozzle holding parts, so as to minimize a moving range and enable a pipette action for preventing contamination.

18 Claims, 4 Drawing Sheets

BIOCHEMICAL TREATMENT DEVICE WITH DISPENSING UNIT

BACKGROUND OF THE INVENTION

1. Field of the Invention

The present invention relates to a biochemical reaction treatment device, and more particular to a nucleic acid specimen treatment device for testing existence of genes derived from disease germs in a sample such as blood.

2. Description of the Related Art

Many methods are proposed which adopt a hybridization reaction using a probe carrier represented by a DNA microarray as a method for quickly and precisely analyzing a base sequence of nucleic acids and detecting target nucleic acids in a nucleic acid specimen. To obtain the DNA microarray, a probe having a base sequence complementary to the target nucleic acids is fixed on a solid phase such as a bead and a glass plate with high density, and a method for detecting the target nucleic acids using the DNA microarray generally has following steps.

In a first step, the target nucleic acids are amplified by an amplification method represented by a PCR method. Concretely, first and second primers are first added to the nucleic acid specimen, and a temperature cycle is applied (hereinafter referred to as "1st PCR"). The first primer is specifically bounded with some of the target nucleic acids, and the second primer is specifically bounded with some of the nucleic acids complementary to the target nucleic acids. When double-stranded nucleic acids including the target nucleic acids are bounded with the first and second primers, the double-stranded nucleic acids including the target nucleic acids are amplified by an elongation reaction.

After the double-stranded nucleic acids including the target nucleic acids are amplified sufficiently, substances other than amplified double-stranded nucleic acids such as non-reacted primers and fragments of nucleic acids are removed by purification. Methods for adsorbing the double-stranded nucleic acids to magnetic particles or methods using a column filter are known as a purification method.

After completion of purification, a third primer is added to the nucleic acid specimen, and the temperature cycle is applied (hereinafter referred to as "2nd PCR"). The third primer is marked with an enzyme, a fluorescent material, a luminescent material or the like, and is specifically bounded with some of the nucleic acids complementary to the target nucleic acids. When the third primer is bounded with the nucleic acids complementary to the target nucleic acids, the target nucleic acids marked with the enzyme, the fluorescent material, the light-emitting material or the like are amplified by the elongation reaction. As a result, when the nucleic acid specimen includes the target nucleic acids, the marked target nucleic acids are generated, and when the nucleic acid specimen does not include the target nucleic acids, the marked target nucleic acids are not generated.

In a second step, the nucleic acid specimen is brought into contact with the DNA microarray, and is hybridized with the probe of the DNA microarray. Concretely, the temperatures of the DNA microarray and the nucleic acid specimen are increased. If there is any target nucleic acid complementary to the probe, the probe and the target nucleic acids form a hybrid material.

In a third step, the target nucleic acids are detected. For example, when the maker materials are fluorescent materials, the fluorescent materials are excited by a laser and the like to measure a luminance thereof. That is to say, whether the probe and the target nucleic acids form the hybrid material or not can be detected by marker materials of the target nucleic acids, thereby confirming a specific base sequence.

Such a DNA microarray utilizing this hybridization reaction is expected for application to a medical diagnosis for specifying the disease germs and a gene diagnosis for testing constitutions of patients. A diagnosis method using such a DNA microarray utilizes a few kinds of liquids while exchanging disposable pipette tips at a pipette tip. Therefore, this operation is very complicated, and a treatment capability is limited in a manual operation. To solve these problems, some devices are proposed which automate an amplification step, a hybridization step, a detection step and a dispensing step for moving and mixing the liquid.

Now, one example of a DNA testing device is shown in FIG. 5. In FIG. 5, a constitution using one pipette is shown. A DNA testing device 101 comprises a dispensing unit 102, a base 108, a pipette tip case 110, an amplification plate 120 and a hybridization plate 130. The dispensing unit 102 can freely move in a space in the device by Z-direction moving means 104, X-direction moving means 105, and Y-direction moving means 106 and 107. Here, the Z-direction is defined as a direction perpendicular to an XY-plane in FIG. 5. Also, the dispensing unit 102 has a nozzle holding part 103, and the nozzle holding part 103 is fitted with a pipette tip 111. The pipette tip is mounted by moving the nozzle holding part 103 to the pipette tip 111 of the pipette tip case 110. The dispensing unit 102 to which the pipette tip 111 is mounted can move the liquid contained in a well 121 of an amplification plate 120 or a well 131 of a hybridization plate 130 by a pipette mechanism (not shown) to another well. The liquid is moved and mixed, and temperature control means (not shown) controls the temperature of the liquid, so that a biochemical reaction can be promoted.

The constitution using only one pipette as shown in FIG. 5 requires considerable times to treat a plurality of samples even in the case of an automated device. Therefore, as described in Japanese Patent Application Laid-Open Nos. H09-96643 and 2003-274925, devices for simultaneously treating a plurality of samples with a plurality of pipettes have been proposed.

In the constitutions described in Japanese Patent Application Laid-Open Nos. H09-96643 and 2003-274925, an action that the pipette treating a certain sample passes on the well holding a reagent for another sample may be inevitable. During movement of the reagent, the liquid held in the pipette tip might drop as micro-droplets due to vibrations and the like of a carrying shaft. When the liquid including the other sample is mixed with the reagent, it becomes a cause of misjudgment at the time of diagnosis.

SUMMARY OF THE INVENTION

An object of the present invention is to provide a biochemical treatment device capable of effectively preventing contamination in light of the above-mentioned problems.

A biochemical treatment device of the present invention comprises a base stand capable of mounting a reaction unit with a plurality of lines of reaction area arranged at predetermined pitches so as to simultaneously treat a plurality of samples, wherein a plurality of lines of the reaction area are allocated to the same sample; a plurality of nozzles arranged at predetermined pitches in a direction perpendicular to said lines of reaction area; a dispensing unit holding the nozzles, wherein the width of said lines of reaction area is narrower than the pitch of the nozzles; and a moving mechanism relatively moving the base stand and the dispensing unit.

Further features of the present invention will become apparent from the following description of exemplary embodiments with reference to the attached drawings.

DESCRIPTION OF THE EMBODIMENTS

Now, embodiments of the present invention will be described with reference to the drawings.

Following is an embodiment, in which the present invention is applied when existence and volume of target nucleic acids (DNA) in a nucleic acid specimen are determined using a unit for a PCR as a reaction unit, a DNA microarray as a testing unit, and a pipette tip as a nozzle.

Figure 1:
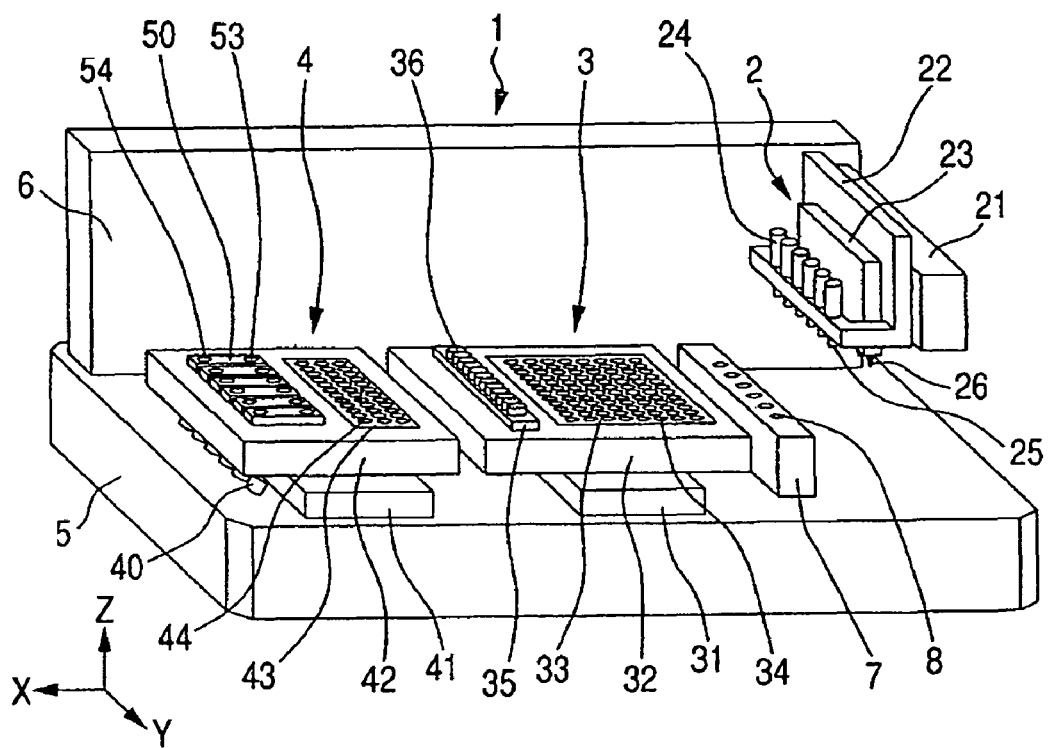
FIG. 1 is a perspective view for explaining the structure of an automatic DNA testing device in an embodiment of the present invention.
Figure 2:
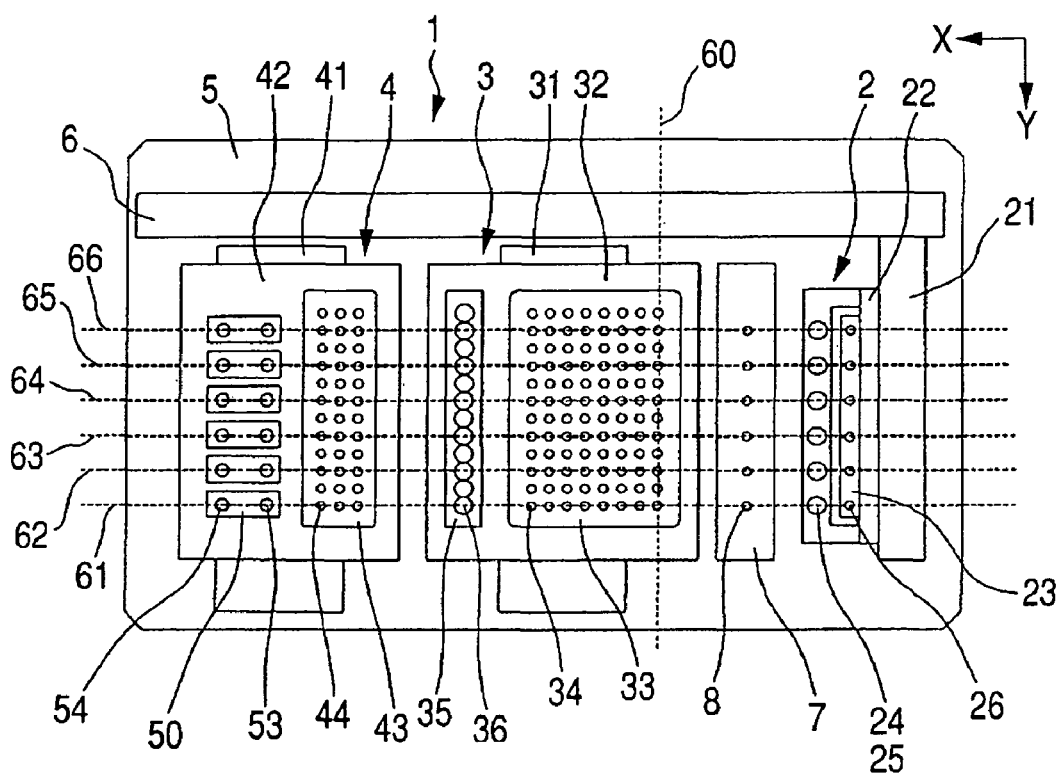
FIG. 2 is a first plane view for explaining the action of an automatic DNA testing device in an embodiment of the present invention.
Figure 3:
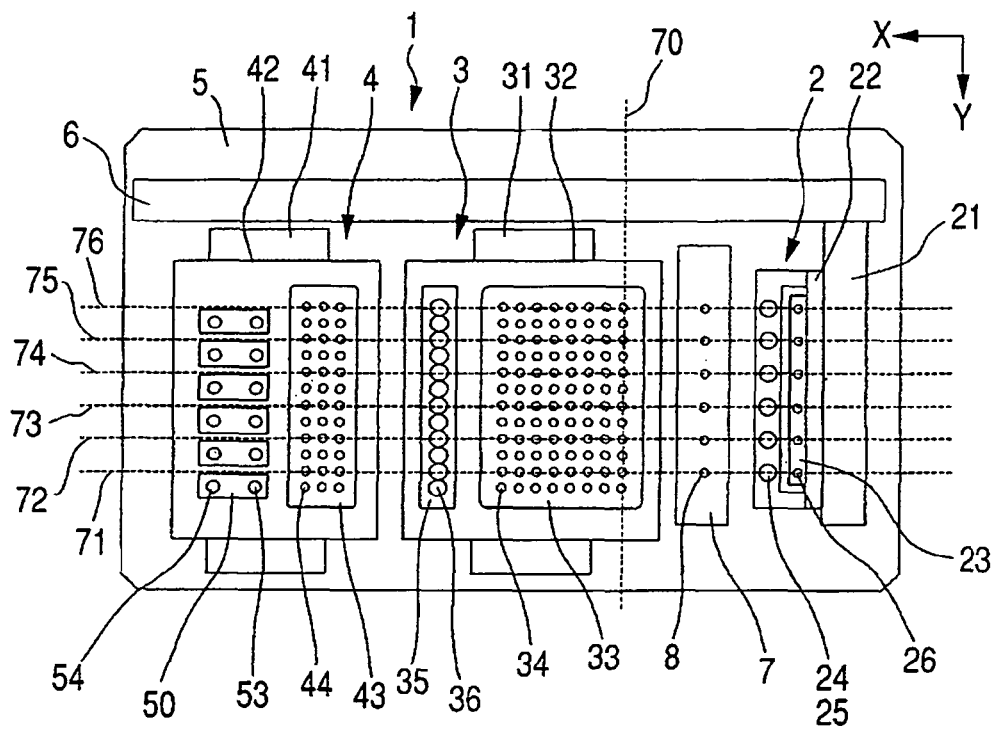
FIG. 3 is a second plane view for explaining the action of an automatic DNA testing device in an embodiment of the present invention.

FIG. 1 is a perspective view for explaining the structure of an automatic DNA testing device in an embodiment of the present invention. FIGS. 2 and 3 are plane views for explaining the action of an automatic DNA testing device in an embodiment of the present invention.

First, the structure of the automatic DNA testing device will be explained with reference to FIG. 1. An automatic DNA testing device 1 has a constitution that a dispensing unit 2, an amplification unit 3 and a hybridization unit 4 are arranged on a base 5. Also, a sample stage 7 in which a sample solution to be tested is placed is provided on an upstream side of the amplification unit 3.

The dispensing unit 2 is supported by a mechanism capable of the movement of the dispensing unit in an X-direction (hereinafter referred to as "an X-shaft 6"), and an arm capable of the movement of the dispensing unit in a Z-direction (hereinafter referred to as "a Z-shaft 21"). In this manner, the dispensing unit 2 can move in a space on the amplification unit 3 and the hybridization unit 4 in an XZ-direction. The illustrated device comprises nozzle moving means having the dispensing unit 2, the X-shaft 6 of the dispensing unit, and the Z-shaft 21 of the dispensing unit. Also, the amplification unit 3 constitutes a reaction unit, and the hybridization unit 4 constitutes a testing unit. A mechanism utilized in various treatment machines and reaction devices can be used for each moving means of this device. For example, a mechanism using a guide for restraining a moving direction, a belt or roller capable of moving an arm, stand or the like along the guide, and drive means thereof can be utilized.

In the dispensing unit 2, pipette mechanisms 24 are fixed to a housing 22, and nozzle holding parts 25 capable of mounting the pipette tips are provided at the tips of the pipette mechanisms 24. The nozzle holding parts 25 are aligned at equal pitches in the Y-direction. When the pipette mechanisms 24 are driven, liquid can be introduced in the pipette tips mounted to the nozzle holding parts 25, or the liquid can be discharged from the pipette tips. A boring Z-shaft 23 is mounted to the housing 22 of the dispensing unit 2, and boring mechanisms 26 are aligned at the tip of the boring Z-shaft 23 at pitches same as those of the nozzle holding parts 25 in the Y-direction. Thereby, regardless of drive of the dispensing unit 2 in the Z-direction, the boring mechanisms 26 can be independently driven in the Z-direction. That is to say, the boring mechanisms 26 can be arranged above or below the nozzle holding parts 25. The number of the boring mechanisms 26 is equal to that of the nozzle holding parts 25, and the positions in the Y-direction are equal to each other. Therefore, holes can be bored at positions for dispensing the liquid with the nozzle holding parts 25.

The amplification unit 3 has a constitution that an amplification stage 32 as an installation stand is mounted on the Y-shaft 31 of the amplification unit as relative moving means. The amplification stage 32 can move in the Y-direction by the Y-shaft 31 of the amplification unit. An amplification plate 33 and a pipette tip case 35 can be arranged on the amplification stage 32. The amplification plate 33 is a commercially available 96-well plate made of polypropylene with 8×12 amplification wells 34. The amplification wells 34 are filled with a reagent and a cleansing liquid used in a first PCR step (1st PCR), a purification step and a second PCR step (2nd PCR) in advance. In a stage, in which the amplification plate is mounted in the device, a protective sheet (not shown) for preventing mixture of contaminants into each of the amplification wells 34 is adhered on the top face of the amplification plate to cover opening faces of the respective amplification wells 34. Twelve pipette tips 36 are accommodated in one line in the Y-direction in the pipette tip case 35. Here, a line of the 12 amplification wells 34 is matched with a line of the 12 pipette tips 36 in the Y-direction. Also, the pipette tip case 35 may be installed to at least one of the stages 32 and 42, the amplification unit 3 and the hybridization unit 4.

The hybridization unit 4 has a constitution that the hybridization stage 42 as an installation stand is mounted to the Y-shaft 41 of the hybridization unit as relative moving means. The hybridization stage 42 can move in the Y-direction by the Y-shaft 41 of the hybridization unit. A hybridization plate 43 and cassettes 50 can be arranged on the hybridization stage 42. The hybridization plate 43 is cut out of a commercially available 96-well plate made of polypropylene with 3×12 hybridization wells 44.

Then, the action of the automatic DNA testing device according to the present invention will be explained with reference to FIGS. 2 and 3. The action for mounting the pipette tips will be first described. This action starts from a condition that the pipette tips are not mounted to the nozzle holding parts 25. As shown in FIG. 2, the amplification stage 32 is moved to locate the pipette tips 36 on lines 61 to 66. Thereby, Y-coordinates of the nozzle holding parts 25 and the pipette tips 36 are matched with each other. Then, the X-shaft 6 of the dispensing unit is moved so that the X-direction positions of the nozzle holding parts 25 and the pipette tips 36 are matched with each other, and the dispensing unit 2 is lowered by the Z-shaft 21 of the dispensing unit. Thereby, the nozzle holding parts 25 are fitted with the pipette tips 36. The 6 nozzle holding parts 25 with the identical shape are aligned in the Y-direction at equal pitches, and the 12 pipette tips 36 are aligned in the Y-direction at half pitches of the nozzle holding parts 25. By this action, the pipette tips 36 are mounted to all of the 6 nozzle holding parts 25. Here, the number of the nozzle holding parts 25 is, but not limited to, designated as 6, and a desired number more than one of the nozzle holding parts may be aligned in the Y-direction. Furthermore, although the nozzle holding parts 25, but not must be, are aligned at equal pitches, the pipette tips 36 accommodated in the pipette tip case 35 may be arranged at positions corresponding to the nozzle holding parts 25. When this constitution is explained with reference to FIG. 2, the dispensing unit 2 having 3 nozzle holding parts 25 arranged only on the lines 61, 62 and 65 may do.

The boring mechanisms 26 are arranged above the nozzle holding parts 25 by the boring Z-shaft 23. Thereby, at the time of mounting the pipette tips, the boring mechanisms 26 do not collide with the amplification stage 32 and the like to block the action. Finally, the dispensing unit 2 is raised by the Z-shaft 21 of the dispensing unit, so that the pipette tips 36 fitted with the nozzle holding parts 25 are detached from the pipette tip case 35.

The action for removing the pipette tips will be explained. For example, when the pipette tips 36 on the lines 61 to 66 shown in FIG. 2 are used, accommodation parts of the pipette tip case 35 on the lines 61 to 66 shown in FIG. 2 are vacant. The used pipette tips are brought back to the vacant accommodation part of the pipette tip case 35. The X-shaft 6 of the dispensing unit and the Z-shaft 21 of the dispensing unit are driven, so that the pipette tips mounted to the nozzle holding parts 25 are inserted in a vacant portion of the accommodation part of the pipette tip case 35. The pipette tips are detached from the nozzle holding parts 25 by a pipette tip ejecting mechanism (not shown) provided to the dispensing unit 2. Concretely, by pushing only the pipette tips downward, the nozzle holding parts 25 are disengaged from the pipette tips. Finally, the dispensing unit 2 is raised by the Z-shaft 21 of the dispensing unit, so as to finish the pipette tip removing action.

The boring action will be now explained. A protective sheet (not shown) is adhered on the top faces of the amplification plate 33 and the hybridization plate 43 to prevent mixture of contaminants. Therefore, when the reagent and the cleansing liquid contained in the amplification wells 34 and the hybridization wells 44 are used, it is required to bore the protective sheet. One example, when the 6 amplification wells 34 are bored where the X-direction is on the line 60 and the Y-direction is on the lines 61 to 66 in FIG. 2, will be explained. First, the boring mechanisms 26 are brought below the pipette tips mounted to the nozzle holding parts 25 by the boring z-shaft 23. Thereby, the pipette tips mounted to the nozzle holding parts 25 do not touch the amplification stage 32 and the like. As shown in FIG. 2, the amplification stage 32 is moved by the Y-shaft 31 of the amplification unit, so that the amplification wells 34 to be bored are located on the lines 61 to 66. Thereafter, the X-shaft 6 of the dispensing unit is driven, so that the boring mechanisms 26 are matched with the line 60. Under this condition, when the Z-shaft 21 of the dispensing unit is lowered, the boring mechanisms 26 project through the protective sheet on the top face of the amplification plate 33, so as to bore the top faces of the 6 amplification wells 34. Finally, the dispensing unit 2 is raised by the Z-shaft 21 of the dispensing unit and the boring mechanisms 26 are drawn from the amplification plate 33, so as to complete the boring action.

The dispensing action will be explained. One example, when the sample solution contained in the sample wells 8 arranged on the sample stage 7 is moved to the 6 amplification wells 34 where the X-direction is on the line 60 and the Y-direction is on the lines 61 to 66 in FIG. 2, will be explained. First, the boring mechanisms 26 are brought above the nozzle holding parts 25 by the boring Z-shaft 23, so as to prevent the boring mechanisms 26 from colliding with the amplification stage 32 and the like to block the action. As shown in FIG. 2, the amplification stage 32 is moved by the Y-shaft 31 of the amplification unit, so that the amplification wells 34 for dispensing the solution are located on the lines 61 to 66. The X-shaft 6 of the dispensing unit and the Z-shaft 21 of the dispensing unit are driven, so that the tips of the pipette tips mounted to the nozzle holding parts 25 are brought into contact with the sample solution in the sample wells 8. The pipette mechanisms 24 are actuated, so as to introduce the sample solution in the pipette tips. Under a condition that the sample solution is held in the pipette tips, the Z-shaft 21 of the dispensing unit is driven to remove the pipette tips from the sample wells 8. The X-shaft 6 of the dispensing unit is driven, so that the nozzle holding parts 25 are matched with the line 60. The tips of the pipette tips mounted to the nozzle holding parts 25 are inserted in the amplification wells 34 by the Z-shaft 21 of the dispensing unit. The pipette mechanisms 24 are actuated to discharge the sample solution in the pipette tips to the amplification wells 34, so that the sample solution is mixed with the reagent contained in the amplification wells 34. Finally, the dispensing unit 2 is raised by the Z-shaft 21 of the dispensing unit and the pipette tips are drawn from the amplification plate 33, so as to complete the dispensing action.

Now, the reagent and the cleansing liquid held by the amplification plate 33 and the hybridization plate 43 will be explained. The reagent and the cleansing liquid required for treating the same sample (first sample) are contained in the amplification wells 34 and the hybridization wells 44 on the line 61 shown in FIG. 2 and on the line 71 shown in FIG. 3. Some of these wells are used for mixture-treatment, PCR reaction treatment and purification of the reagent and the cleansing liquid. The reagent and the cleansing liquid are moved from the wells storing the reagent and the cleansing liquid to the treatment wells by the dispensing unit 2. As is similar to the lines 61 and 71, the reagent and the cleansing liquid are also contained in the amplification wells 34 and the hybridization wells 44 on the lines 62 to 66 shown in FIG. 2 and on the lines 72 to 76 shown in FIG. 3. Each of the wells forming two adjacent lines is arranged to treat the same samples (second to sixth samples). Thereby, a plurality of samples (first to sixth samples) can be identically processed concurrently. The reagent and the cleansing liquid used for the same sample are located in two lines, because there are many kinds of reagents and cleansing liquids. The two lines of the reagent and the cleansing liquid can restrain the X-direction length of the device. In this case, although the number of lines is two, the number may be one, or three or more. When the second line is used, the amplification stage 32 or the hybridization stage 42 may be moved in the Y-direction by pitches of the amplification wells 34 or the hybridization wells 44 from a condition shown in FIG. 2 to a condition shown in FIG. 3.

While the above-mentioned pipette-tip-mounting, pipette-tip-removing, boring and dispensing actions are done, each of amplification, purification and hybridization steps is promoted. According to the order of the steps, the actions of the device will be explained with reference to FIGS. 1 to 3.

First, the sample wells 8 containing the sample solution are arranged on the sample stage 7. The amplification plate 33, the pipette tip case 35, the hybridization plate 43 and the cassettes 50 to be used are set on the DNA testing device 1. Here, when the DNA testing device 1 is started, a DNA testing step is started.

The pipette tips 36 are first mounted to the nozzle holding parts 25. Then, the top faces of the amplification wells 34 containing a 1st PCR reagent are bored, and the sample solution is moved to the amplification wells 34 containing the 1st PCR reagent from the sample wells 8 by the dispensing unit 2. After the 1st PCR reagent is mixed with the sample solution, a temperature cycle is applied to the amplification wells 34 containing mixture solution by temperature control means (not shown), thereby promoting the 1st PCR.

After completion of the 1st PCR, the step goes to the purification step for removing contaminants other than nucleic acids. Magnetic particles specifically adsorbing the nucleic acids are put in the amplification wells 34 for purification treatment. 1st PCR products are moved to the amplification wells 34 containing the magnetic particles, so as to adsorb the nucleic acids to the magnetic particles. The magnetic particles are fixed on the bottom faces of the amplification wells 34 by magnetic force generation means (not shown), and the solution in the wells is removed by the dispensing unit 2. Furthermore, the magnetic particles are cleansed with a plurality of cleansing liquids several times. The cleansing liquid is moved to the amplification wells 34 containing the magnetic particles by the dispensing unit 2, and mixed while a magnetic force is not applied. The magnetic particles are fixed on the bottom faces of the amplification wells 34 by magnetic force generation means (not shown), and the used cleansing liquid is removed by the dispensing unit 2.

After completion of cleansing the magnetic particles, the nucleic acids are removed. Mixture of contaminants leads to bad influences on judgment. If the pipette tips used until that time continue to be used, contaminants adhered to the pipette tips might be mixed. Therefore, in the purification step, it is preferable to exchange pipette tips. In exchanging the pipette tips, the pipette tips may be returned to a vacant accommodation part of the pipette tip case 35, and the unused pipette tips 36 may be mounted to the nozzle holding parts 25.

Eluate is moved to the amplification wells 34 containing the magnetic particles by new pipette tips. Adsorption of the nucleic acids to the magnetic particles is released by the eluate. The magnetic particles are fixed on the bottom faces of the amplification wells 34 by magnetic force generation means (not shown), and the solution containing the nucleic acids is moved by the dispensing unit 2, thereby completing the purification step.

The solution after the purification step is mixed with a 2nd PCR reagent contained in the amplification wells 34, and a temperature cycle is applied by temperature regulation means (not shown), thereby promoting the 2nd PCR. When the temperature cycle is finished, the amplification step is completed. By the 2nd PCR, when the target nucleic acids are amplified in the 1st PCR, fluorescent markers are given to them.

Figure 4A:
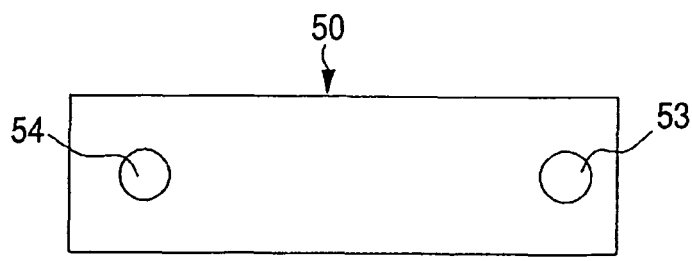
FIGS. 4A and 4B show plane views and cross section views for explaining cassettes in embodiment of the present invention.
Figure 4B:
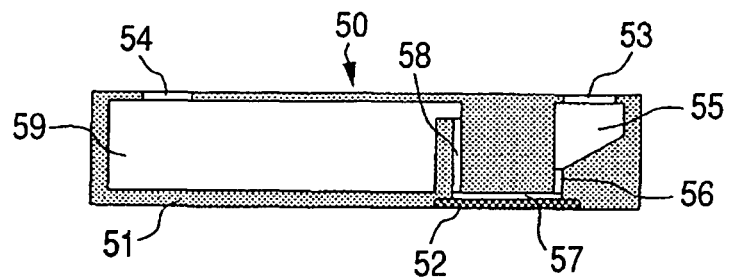
Figure 5:
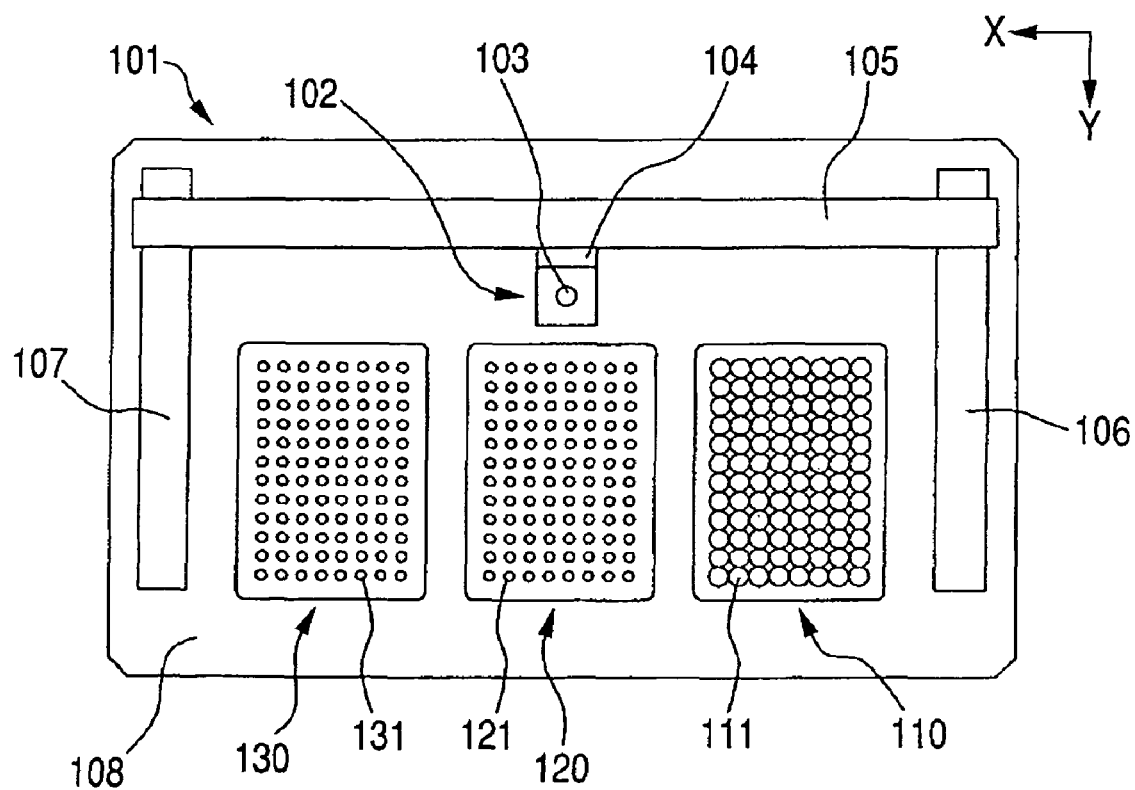
FIG. 5 is a plane view for explaining the structure of an automatic DNA testing device of a prior art.

The liquid containing amplification products is moved to the hybridization wells 44 containing the hybridization reagent by the dispensing unit 2. After the amplification products are mixed with the hybridization reagent, mixture liquid thereof is moved to the cassettes 50. FIG. 4A shows a plane view of the cassettes, and FIG. 4B shows a cross section view of the cassettes. The cassette 50 comprises a housing 51 and a DNA microarray 52. Injection ports 53 are bored on the top faces of the cassettes 50, from which the mixture liquid is dispensed to a liquid storage chamber 55 by the dispensing unit 2. Suction ports 54 are provided on opposite sides of the injection ports 53, with which suction mechanisms (not shown) are brought into close contact to suck the air. Then, the mixture liquid is introduced to a reaction chamber 57 through a flow path 56. Thereby, the mixture liquid can be brought into contact with the DNA microarray 52. Furthermore, the temperature of the mixture liquid in the reaction chamber 57 is raised by temperature regulation means (not shown), so as to promote the hybridization reaction.

After completion of the hybridization reaction, the air is further drawn from the suction ports 54. Then, the mixture liquid moves through a flow path 58 to a waste chamber 59. The surface of the DNA microarray 52 is then cleansed. The hybridization wells 44 hold several kinds of cleansing liquids. The cleansing liquids are carried to the liquid storage chamber 55 of the cassette 50 by the dispensing unit 2 and the air is drawn from the suction ports 54, so that the cleansing liquids pass through the surface of the DNA microarray 52. The cleansing liquids move to the waste chamber 59, and do not leak to outside of the cassettes 50. By repeating this several times, the surface of the DNA microarray 52 is completely cleansed.

After completion of the hybridization reaction, a detection system 40 arranged below the hybridization stage 42 judges existence and volume of the reaction between the target nucleic acids and probe nucleic acids fixed to the DNA microarray. As in the above-mentioned example, when fluorescent marker is given to the target nucleic acids, lights exciting the fluorescent markers are radiated to the DNA microarray, so as to measure fluorescence or fluorescent volume at each of probe fixing spots. If the detection system 40 detects the fluorescence or fluorescent volume, the cassettes 50 have optical paths capable of radiating excitation lights and measuring fluorescence. Existence or volume of target substances in the sample is obtained on the basis of data relating to the resultant fluorescence. Herein, although the detection system 40 is arranged below the hybridization stage 42, the detection system 40 may be arranged in a testing space separately installed in the device and the cassettes 50 may be conveyed to the testing space by a conveying arm. Furthermore, the detection system may be arranged to the other detecting device and the cassettes 50 after the hybridization reaction may be removed and set to the detecting device.

All or desired parts of each of the above-explained actions can be automatically performed by a program preinstalled to a computer mounted to the device or having a structure mountable to the device.

As described above, if the width of the amplification well lines and the hybridization well lines used for the same sample is made narrower than nozzle pitches, when pipette tip treating this sample moves along these well lines, the pipette tip does not pass above the other well lines holding the reagent for the other sample. Or, the pipette tip adjacent to this pipette tip for treating the other sample does not pass on the target well lines of the first-described pipette tip. Herein, one example, when the nozzle pitches are equal to each other, is described, but even when the nozzle pitches are not equal, the width of the amplification well lines and the hybridization well lines used for the same sample is made to fall within an area smaller than the narrowest width of the nozzle pitches, so that a similar effect can be obtained.

Such a pipette action can prevent contamination due to drop of droplets. Also, under a condition that the pipette tip case is placed on the well lines and the pipette tips are prepared for the case, the width of the pipette tips used for the same sample in a nozzle arranging direction is made to fall within an area narrower than the nozzle pitches, so that a risk of contamination to unused chips can be effectively eliminated. When many kinds of reagents are required, the size of the device can be restrained by locating reaction wells in a plurality of lines. Furthermore, because the reaction wells used for the same sample are arranged all together, the moving distance of the pipette tips can be restrained small, and the tact of the dispensing step can be shortened. Also, because a plurality of reaction units are provided with independent reaction unit moving means, a plurality of reactions can be made concurrently, so as to improve treatment capacity of the automatic DNA testing device.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims priority from Japanese Patent Application No. 2005-291770 filed on Oct. 4, 2005, which is hereby incorporated by reference herein.

What is claimed is:

1. A biochemical treatment device comprising:
a dispensing unit holding a plurality of nozzles arranged at a first pitch P1 in a first direction, wherein the dispensing unit can move to a position in a second direction; and
the following two stages (1) and (2) aligned in the second direction and used for a treatment using the dispensing unit:
(1) a first stage to place a plurality of samples arranged at the first pitch P1 in the first direction; and
(2) a second stage on which a well plate is to be placed, wherein the well plate has a matrix of wells in the first direction and in the second direction, wherein pitches of the wells in the first direction are arranged at a second pitch P2, wherein P2 is defined as a pitch of the wells in the first direction, where P2=P1/n, and n is an integer other than 1, wherein the second stage moves in a manner such that one of the nozzles applied for a sample does not pass over a well in which another sample is to be treated and the plurality of samples are dispensed into the wells by moving the second stage, and wherein each of 2 to n numbers of adjacent well lines treats only one of the arranged samples.

2. The biochemical treatment device of claim 1, wherein the dispensing unit does not move into the first direction.

3. The biochemical treatment device of claim 1, wherein n is 2.

4. The biochemical treatment device of claim 1, wherein the second stage moves in a distance range that is narrower than P1.

5. The biochemical treatment device of claim 1, wherein the first direction is perpendicular to the second direction.

6. The biochemical treatment device of claim 1, wherein a variety of samples are placed in the first stage.

7. The biochemical treatment device of claim 1, further comprising a third stage, wherein a plurality of cassettes with nucleic acid microarrays are to be placed on the third stage, and wherein the plurality of cassettes are to be arranged in the first direction at the first pitch P1.

8. The biochemical treatment device of claim 7, wherein the third stage can move in the first direction independently from the second stage.

9. The biochemical treatment device of claim 1, wherein the second stage can move in the first direction.

10. A biochemical treatment apparatus comprising:
a first stage for holding a plurality of samples which are linearly arranged at a first pitch P1; and
a movable dispensing unit having an array of a plurality of nozzles linearly arranged at the first pitch P1, wherein the dispensing unit is capable of taking the plurality of samples out; and
a movable second stage to place a matrix of wells in a first direction and in a second direction, wherein the second stage can move in the first direction,
wherein a pitch P2 is defined as a pitch of the wells linearly arranged in the first direction and is equal to P1/n where n is an integer other than 1,
wherein the dispensing unit supplies the plurality of samples into the matrix of wells,
wherein each of the samples is treated in the wells arranged in adjacent n lines respectively among the matrix of the wells,
wherein the second stage moves in a manner such that one of the nozzles applied for a sample does not pass over a well in which another sample is to be treated, and
wherein a direction of the arrangement of the nozzles aligns with the first direction when the nozzles are passing over the second stage.

11. The biochemical treatment device of claim 10, wherein the dispensing unit moves in the second direction.

12. The biochemical treatment device of claim 10, wherein the dispensing unit does not move into the first direction.

13. The biochemical treatment device of claim 10, wherein n is 2.

14. The biochemical treatment device of claim 10, wherein the second stage moves in a distance range that is narrower than P1.

15. The biochemical treatment device of claim 10, wherein the first direction is perpendicular to the second direction.

16. The biochemical treatment device of claim 10, wherein a variety of samples are placed on the first stage.

17. The biochemical treatment device of claim 10, further comprising a third stage, wherein a plurality of cassettes with nucleic acid microarrays are to be placed on the third stage, and wherein the plurality of cassettes are to be arranged at the first pitch P1.

18. The biochemical treatment device of claim 17, wherein the third stage can move in the first direction independently from the second stage.

* * * * *